(12) United States Patent
Schonbrun et al.

(10) Patent No.: US 10,852,295 B2
(45) Date of Patent: *Dec. 1, 2020

(54) EVANESCENT HEMOLYSIS DETECTION

(71) Applicant: Instrumentation Laboratory Company, Bedford, MA (US)

(72) Inventors: Ethan Schonbrun, Newton, MA (US); Gert Blankenstein, Dortmund (DE); Josef Kerimo, Concord, MA (US); Hansong Zeng, Lowell, MA (US)

(73) Assignee: Instrumentation Laboratory Company, Bedford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/383,427

(22) Filed: Apr. 12, 2019

(65) Prior Publication Data
US 2019/0234931 A1    Aug. 1, 2019

Related U.S. Application Data

(63) Continuation of application No. 15/594,827, filed on May 15, 2017, now Pat. No. 10,288,600.
(Continued)

(51) Int. Cl.
*G01N 33/49*    (2006.01)
*G01N 21/05*    (2006.01)
(Continued)

(52) U.S. Cl.
CPC .............. *G01N 33/49* (2013.01); *B01L 3/502* (2013.01); *G01N 21/0303* (2013.01);
(Continued)

(58) Field of Classification Search
CPC ...... G01N 21/05; G01N 21/25; G01N 21/552; G01N 21/0303; G01N 33/49; B01L 3/502
(Continued)

(56) References Cited

U.S. PATENT DOCUMENTS

| 4,818,710 | A | * | 4/1989 | Sutherland | ........... G01N 21/648 |
| | | | | | 250/227.23 |
| 5,331,958 | A | * | 7/1994 | Oppenheimer | .... A61B 5/14535 |
| | | | | | 356/39 |

(Continued)

FOREIGN PATENT DOCUMENTS

CN    104136911 A    11/2014
EP    2793015 A1    10/2014
(Continued)

OTHER PUBLICATIONS

International Preliminary Report on Patentability of corresponding PCT Application No. PCT/US2017/032613 filed Nov. 20, 2018 (8 pages).
(Continued)

*Primary Examiner* — Roy M Punnoose
(74) *Attorney, Agent, or Firm* — Burns & Levinson, LLP; Joseph P. Quinn (57) ABSTRACT

Analyte content in a cell free portion of a body fluid, such as blood, is optically determined without centrifugation or other preliminary steps for separating the cell free portion from the body fluid. A channel is configured for containing a flowing sample of the body fluid along an optical boundary. The channel is configured so that a cell free layer of the fluid naturally forms along the boundary of the channel which coincides with the optical boundary. A light source is directed onto the optical boundary at an angle selected to generate total reflection from the boundary and to generate an evanescent field across the boundary in the cell free layer of fluid. A light detector is configured to detect absorption of the light in the evanescent field. The light source and light detector are matched to the wavelength range of an absorption peak of the analyte being detected.

18 Claims, 6 Drawing Sheets

Related U.S. Application Data (60) Provisional application No. 62/339,269, filed on May 20, 2016.

(51) Int. Cl.
*G01N 21/552* (2014.01)
*B01L 3/00* (2006.01)
*G01N 21/03* (2006.01)
*G01N 21/25* (2006.01)

(52) U.S. Cl.
CPC ............ *G01N 21/05* (2013.01); *G01N 21/25* (2013.01); *G01N 21/552* (2013.01); *B01L 2300/0654* (2013.01); *B01L 2300/168* (2013.01); *G01N 2201/0612* (2013.01)

(58) Field of Classification Search
USPC ......................................................... 356/39
See application file for complete search history.

(56) References Cited

U.S. PATENT DOCUMENTS

| | | | | |
|---|---|---|---|---|
| 5,633,724 | A * | 5/1997 | King .................... | G01N 21/648 356/445 |
| 7,790,464 | B2 * | 9/2010 | Tarasev ................. | G01N 33/721 422/82.05 |
| 8,797,028 | B2 * | 8/2014 | Verschuren ............ | G01N 15/06 324/244 |
| 9,134,223 | B2 * | 9/2015 | Garcia ................... | G01N 21/05 |
| 2007/0046943 | A1 * | 3/2007 | VanWiggeren ....... | G01N 21/553 356/445 |
| 2010/0197038 | A1 * | 8/2010 | Verschuren .......... | G01N 21/552 436/164 |
| 2010/0259254 | A1 * | 10/2010 | Verschuren ............ | G01N 15/06 324/244 |
| 2010/0267163 | A1 * | 10/2010 | Ran ...................... | G01N 21/553 436/164 |
| 2010/0272608 | A1 * | 10/2010 | Penterman ............. | G01K 11/00 422/69 |
| 2010/0328654 | A1 * | 12/2010 | Verschuren .......... | G01N 21/648 356/237.2 |
| 2011/0027916 | A1 * | 2/2011 | Nieuwenhuis .... | B01L 3/502761 436/526 |
| 2011/0188030 | A1 * | 8/2011 | Verschuren ............ | G01N 21/41 356/128 |
| 2012/0170042 | A1 * | 7/2012 | Kahlman ........... | G01N 21/8483 356/436 |
| 2012/0258553 | A1 * | 10/2012 | Dittmer ................ | G01N 27/745 436/501 |
| 2014/0118745 | A1 * | 5/2014 | Neijzen .............. | G01N 21/0303 356/432 |
| 2014/0262831 | A1 * | 9/2014 | Balasubramanian .... | C12Q 1/26 205/778 |
| 2015/0025341 | A1 * | 1/2015 | Sakota ................... | G01N 21/05 600/322 |
| 2015/0338338 | A1 * | 11/2015 | Messerschmidt .... | A61B 5/0075 435/288.7 |
| 2017/0336385 | A1 | 11/2017 | Schonbrun et al. | |

FOREIGN PATENT DOCUMENTS

| | | |
|---|---|---|
| JP | S61191965 A | 8/1986 |
| JP | 2002527136 A | 8/2002 |
| JP | 2011501183 A | 1/2011 |
| JP | 2011232137 A | 11/2011 |
| JP | 2013164372 A | 8/2013 |
| WO | 8801376 | 2/1988 |

OTHER PUBLICATIONS

International Search Report and Written Opinion of corresponding PCT Application No. PCT/US2017/032613, filed May 15, 2017 (15 pages).

A.Q. Liu, et al., "Label-free detection with micro optical fluidic systems (MOFS): a review," vol. 391, No. 7, Anal. Bioanal. Chem., Feb. 2008 (pp. 2443-2452).

Dong et al., "Accurate in situ measurement of complex refractive index and particle size in intralipidemulsions," Journal of Biomedical Optics, 18(8), 7 pages (2013).

Inline Process Refractometer, MISCO Refractometer, 4 pages, https://www.misco.com/refractometers/inline-process-refractometer (May 25, 2016).

Bruls et al., "Rapid integrated biosensor for multiplexed immunoassays based on actuated magnetic nanoparticles," Lab Chip, 9:3504-3510 (2009).

Cattini et al., "A simple measuring system for early detection of haemolysis during haemodialysis," IEEE, 6 pages (2014).

Office Action issued in corresponding Japanese application No. 2018-556988, dated Oct. 29, 2019 (8 pages), and English translation thereto (9 pages).

Second Office Action issued in corresponding Japanese application No. 2018-556988, dated Jul. 22, 2020 (6 pages), and English translation thereto (7 pages).

First Office Action issued in corresponding Chinese application No. 2017800298614, dated Jul. 15, 2020 (9 pages), and English translation thereto (14 pages).

Brian Culshaw et al, "Fiber Optic Sensors", Huazhong University of Science and Technology Press, pp. 200-201, Jul. 31, 1997.

\* cited by examiner

```
┌─────────────────────────────────┐
│  RECEIVE A WHOLE BLOOD SAMPLE   │
│         IN A CHANNEL            │
│              702                │
└─────────────────────────────────┘
                │
┌─────────────────────────────────┐
│  DETECT A FIRST LIGHT SOURCE THROUGH │
│  A PRISM TO THE OPTICAL INTERFACE AT │
│  AN ANGLE OF INCIDENCE GREATER THAN OR│
│  EQUAL TO A CRITICAL ANGLE RELATIVE TO│
│     A NORMAL OF THE INTERFACE    │
│              704                │
└─────────────────────────────────┘
                │
┌─────────────────────────────────┐
│  AIM A FIRST LIGHT DETECTOR TO RECEIVE│
│  THE LIGHT FROM THE FIRST LIGHT SOURCE│
│   THAT HAS BEEN REFLECTED THROUGH │
│   THE PRISM FROM THE OPTICAL INTERFACE│
│              706                │
└─────────────────────────────────┘
                │
┌─────────────────────────────────┐
│ MEASURE ABSORPTION OF THE LIGHT FROM │
│ THE FIRST LIGHT SOURCE BY AN ANALYTES│
│ IN ONLY A PLASMA LAYER OF THE WHOLE │
│   BLOOD SAMPLE WITHIN RANGE OF THE  │
│          EVANESCENT FIELD           │
│              708                │
└─────────────────────────────────┘
```

FIG. 7

EVANESCENT HEMOLYSIS DETECTION

CROSS REFERENCE TO RELATED APPLICATION

This application is a continuation of U.S. application Ser. No. 15/594,827, filed on May 15, 2017 which claims priority to and the benefit of U.S. provisional patent application No. 62/339,269, filed May 20, 2016. The entire contents of which are incorporated herein in their entirety by reference for all purposes.

FIELD OF TECHNOLOGY

Aspects of the present disclosure are directed to the field of clinical analyzers and more particularly to a method and apparatus for measuring free hemoglobin in plasma without separating plasma from a whole blood sample.

BACKGROUND

In a variety of clinical settings, it is important to measure certain chemical characteristics of plasma from whole-blood samples. For example, it is commonly important to measure the analytes, extracellular hemoglobin, bilirubin, and lipid particles in plasma. These settings range from a routine visit of a patient to a physician's office, an emergency room, or monitoring of a hospitalized patient, for example. Numerous techniques and apparatus are commonly used for measuring chemical characteristics of body fluids in clinical settings. Measurement of an analyte in a body fluid sample may be accomplished by numerous methods one of which is by spectroscopic determination.

Some techniques for analyzing body fluid are complex and may involve numerous steps such as centrifugation to prepare a fluid sample for measurement. For example, techniques for measuring analyte content in the plasma portion of a blood sample may involve preliminary steps such as centrifugation of whole blood to separate blood cells from the plasma portion. These preliminary steps add time, complexity and cost to previously known techniques for measuring analyte content in a body fluid.

SUMMARY

The disclosed apparatus and method may be implemented to measure analytes or components in the plasma fraction of a blood sample without any need for separation of plasma from the whole blood sample. Aspects of the present disclosure provide a method and apparatus for quantifying hemolysis in whole blood using frustrated total internal evanescent wave absorption at a prism/blood interface. According to an aspect of the present disclosure, free hemoglobin in a whole blood sample can be measured using evanescent wave absorption without red blood cell separation.

An apparatus for detecting analytes in whole blood without red blood cell separation from the whole blood, the apparatus according to an aspect of the present disclosure includes a channel for receiving a blood sample, and a prism adjacent to the channel. A light source directed through the prism at an angle of incidence greater than or equal to a critical angle relative to a normal of the interface, wherein the angle of incidence creates total internal reflection of light from the first light source and creates an evanescent field extending into the channel. The evanescent field decays to approximately zero within about 1 micron depth into the channel. When whole blood is flowing in the channel, a substantially cell-free plasma layer occupies this thin boundary region of the channel. A light detector is aimed to receive the light from the light source that has been reflected through the prism from an optical interface at the boundary of the channel. Analyte content in a substantially cell-free plasma layer of the blood sample is determined by analysis of the reflected light. One aspect of the present disclosure describes an optical method for quantifying hemolysis in whole blood using frustrated total internal reflection caused by evanescent wave absorption at a prism/blood interface.

BRIEF DESCRIPTION OF THE DRAWINGS

The foregoing will be apparent from the following more particular description of example embodiments of the present disclosure, as illustrated in the accompanying drawings in which like reference characters refer to the same parts throughout the different views. The drawings, which are not necessarily to scale, emphasis illustrative embodiments of the present disclosure.

DETAILED DESCRIPTION

When a whole blood sample flows through a channel having a small cross sectional diameter, such as a blood vessel in the body or a capillary on a chip, for example, the sample behaves as a flow stream in which a substantially cell-free plasma film is present at the edges of the channel. The substantially cell-free plasma film is a very thin layer having a thickness in the range of less than a micron to a few microns at the edge of the channel. It is believed that the substantially cell-free plasma film is present in blood vessels, for example, to help prevent clogging and reduce fluidic resistance of the small blood vessels in the body. The small blood vessels may have cross sectional diameter in a range of about 8 microns, for example.

According to aspects of the present disclosure, absorption of light is measured in the narrow substantially cell free plasma layer at the boundary of the flow channel and an optical interface. To measure the absorption in this narrow region, light is incident onto the boundary at an angle greater than a critical angle. The incident light generates a field, called an evanescent wave, which penetrates into the flow cell. The optical field amplitude of the evanescent wave decays in less than 1 wavelength, approximately 500 nm, from the flow cell surface. Because this optical path-length is so much smaller than typical co-oximetry flow cells (100 um), optical wavelengths corresponding to the maximum hemoglobin absorption, the Soret band around 420 nm, are used instead of typical co-oximetry wavelengths in the range of 500-650 nm.

An evanescent field is an optical field that is created at the boundary of two materials that have a different refractive index, e.g. between a glass prism, and a fluid like blood. The evanescent field exists only next to this interface and decays exponentially as you move away from the boundary. So, far away from the interface, the amplitude of the field goes to zero. Because the evanescent field exists only next to the boundary, the plasma layer next to the boundary can be measured without the field interacting with the cells.

According to an aspect of the present disclosure, the boundary layer is probed with an evanescent field created by total internal reflection from a prism surface. The presence of various analytes in plasma can be measured next to the channel wall without interference from the cells because in the region very close to the wall the plasma is present with no cells.

An evanescent field is generated by configuring the angle of incident light with respect to an axis normal to the boundary to be greater than a certain critical angle by a margin of approximately 1-5 degrees. The critical angle depends on the nature of the two materials on either side of the optical boundary. In an illustrative embodiment in which the optical boundary is formed between a prism made from BK7 glass and blood serum, for example, the critical angle is 62.4 degrees. When the angle of incidence is above the critical angle by a large enough margin, which depends on the light source being used, all of the incident light is reflected. That is called total internal reflection. Under conditions of total internal reflection, the only light on the other side of the boundary is called an evanescent field. On the other hand, when the angle of incidence is less than the critical angle, some of the incident light will propagate into the blood flow.

Because the evanescent light only penetrates a short distance into the channel it provides only a weak absorption signal. Therefore, it is important that the light source emits light in a part of the spectrum that provides good absorption by the analyte being detected. An illustrative embodiment of the disclosed apparatus configured for hemolysis includes a light source that emits light in the 410 nm-420 nm wavelength range because in this range hemoglobin exhibits a very strong absorption peak. In a particular embodiment, a light source that emits light at 405 nm is used for hemolysis. In another embodiment in which the analyte being detected is bilirubin, a light source that emits light with a wavelength of 535 nm may be used. In still another embodiment in which the analyte being detected is lipemia, a light source that emits light with a wavelength of 671 nm may be used.

According to an aspect of the present disclosure, two light sources may be used for hemolysis. Differential detection may be performed by comparing the absorption at the wavelength of a main signal with absorption at some off-resonant wavelength. A first light sources may provide a main signal in the 420 nm wavelength range, for hemolysis. The second light source may be provided in another color to correct for scattering and/or turbidity, or another absorbing analyte. The wavelength of the second light source is not as critical as the wavelength of the first light source. In an illustrative embodiment, the second light source has a wavelength of about 470 nm. Because one or two colors are used in certain embodiments of the disclosed apparatus, the light detectors in these embodiments can be implemented as just one photodiode for each color. It should be understood that the light detectors may alternatively be implemented as spectroscope in alternative embodiments. For example, an embodiment of the disclosed apparatus may be configured with light sources having numerous different wavelengths. In these embodiments absorption may be measured using a spectroscope, for example.

Figure 1:
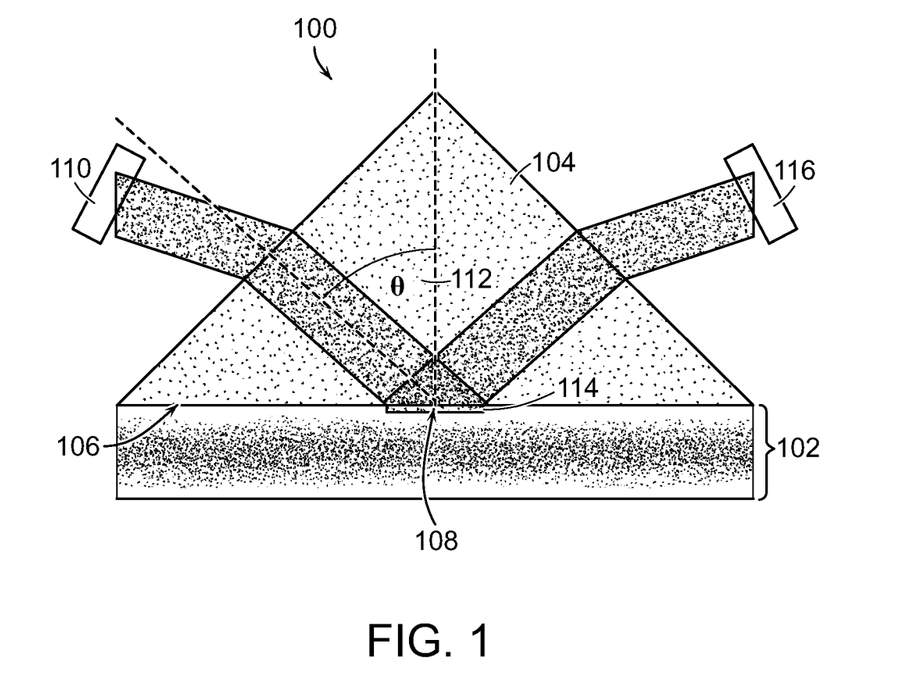
FIG. 1 is an illustration of an apparatus for detecting analytes in whole blood without red blood cell separation from the whole blood according to an aspect of the present disclosure.

Referring to FIG. 1, an apparatus 100 for detecting analytes in whole blood without red blood cell separation from the whole blood according to an aspect of the present disclosure includes a channel 102 for receiving a blood sample and a prism 104 adjacent to the channel 102. The prism 104 includes a first surface 106 abutting the channel 102 and defining an optical interface 108 between the prism 104 and the blood sample when the blood sample is received in the channel 102.

The apparatus 100 also includes a first light source 110 directed through the prism 104 to the optical interface 108 at an angle of incidence 112 greater than or equal to a critical angle relative to a normal axis 114 of the interface. The angle of incidence 112 of optical illumination in the prism 104 is greater than the critical angle of the prism/plasma interface 108. The angle of incidence 112 creates total internal reflection of light from the first light source 110 and creates an evanescent field 114 extending into the channel 102. The evanescent field 114 extends into a plasma layer of the blood sample adjacent to the interface 108 and decays to substantially zero before reaching a portion of the channel 102 containing blood cells.

In an embodiment according to another aspect of the present disclosure, the apparatus 100 may be configured for hemolysis detection in the whole blood. In this embodiment the first light source 110 has an emission wavelength in a range corresponding to a peak in an absorption spectra of hemoglobin. The emission wavelength of the first light source may be between about 410 nanometers and 420 nanometers, for example.

The apparatus 100 also includes a first light detector 116 aimed to receive the light from the first light source 110 that has been reflected through the prism 104 from the optical interface 108. The first light source 110 may include a first light emitting diode and the first light detector 116 may include a first photodiode. In another illustrative embodiment, the first light detector 116 may include a spectroscope, for example.

Comparison circuitry coupled to the first light detector 116 is configured to identify a presence of analytes in the evanescent field 114 by comparing intensity of the light that has been reflected through the prism 104 at a first wavelength with a predetermined intensity. The predetermined intensity may be an intensity of light emitted from the first light source 110, for example. The comparison circuitry may include one or more processors coupled to computer memory, data storage devices and/or communication circuitry and/or one or more computer networks. For example, the comparison circuitry may and may include conventional general purpose computer equipment or dedicated circuitry incorporated with an optical analysis module and configured for measuring and/or comparing signals received by the first light detector. The comparison circuitry may also be configured to output and/or store a measured level of analyte based on the measurements and/or comparisons of the signals received by the first light detector, for example.

Figure 2:
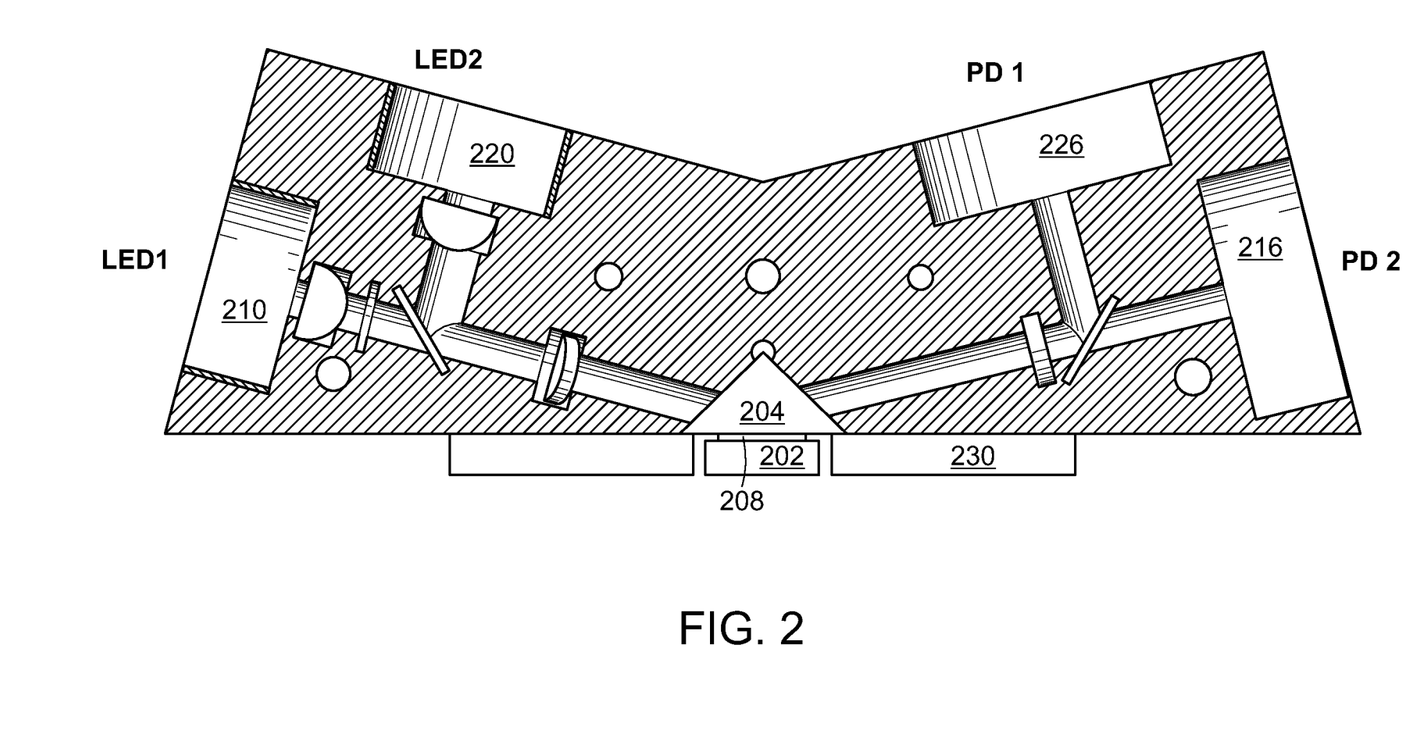
FIG. 2 is an illustration of an apparatus for detecting analytes in whole blood without red blood cell separation from the whole blood according to another aspect of the present disclosure.

Referring to FIG. 2, an apparatus 200 for detecting analytes in whole blood without red blood cell separation from the whole blood according to another aspect of the present disclosure includes a first light source 210 second light source 220 having an emission wavelength different than the emission wavelength of the first light source 210 and directed through the prism 204 to the optical interface 208 at a second angle of incidence greater than or equal to the critical angle relative to the normal of the interface. The second angle of incidence creates total internal reflection of light from the second light source 220 and creates a second evanescent field extending into the channel 202. In this embodiment, the apparatus 200 also includes a second light detector 226 coupled to the comparison circuitry and aimed to receive the light from the second light source 220 that has been reflected through the prism 204 from the optical interface 208. In an illustrative embodiment, the comparison circuitry may be configured to compare the intensity of the light received by the first light detector 216 from the first light source 210 with an intensity of the light received by the second light detector 226 from the second light source 210.

Figure 3:
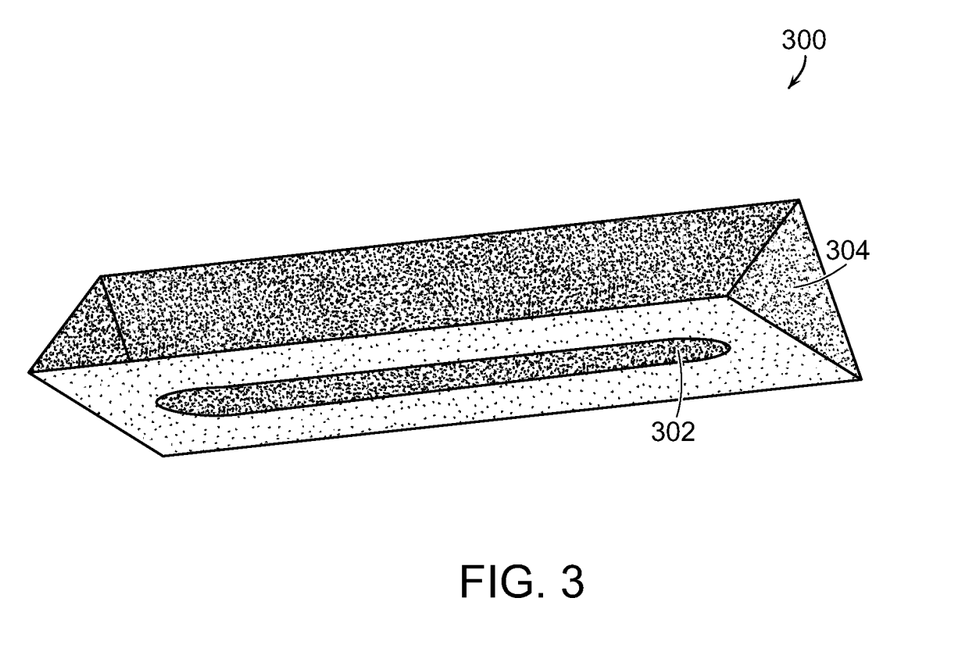
FIG. 3 is an illustration of a prism integrated with a flow cell channel according to another aspect of the present disclosure

In an illustrative embodiment, the flow cell 230 may be a conventional flow cell bonded to a conventional prism 204, for example. The prism 204 may have a rectangular face so that the flow cell 230 can be much longer than the optical path-length through the prism 204. According to aspects of the present disclosure, the prism 204 and/or the flow cell 230 may be made from injection molded plastic or other inexpensive materials, for example. In alternative embodiment according to an aspect of the present disclosure, the apparatus 200 may include a prism 204 in which the channel 202 may be formed within the prism 204. Referring to FIG. 3, the prism 304 in this embodiment includes a flow cell channel 302 that has been patterned into one face of the prism 304 to produce a measurement region inside the prism 304.

An embodiment of the disclosed apparatus may configured as a simple device, having only one or two LEDs or laser diodes as light sources, one or two photo-diodes as light detectors, and a prism. The prism may have an integrated flow cell channel as shown in FIG. 3. In an illustrative embodiment, the entire apparatus could be configured in a package having millimeter scale dimensions, for example.

Figure 4:
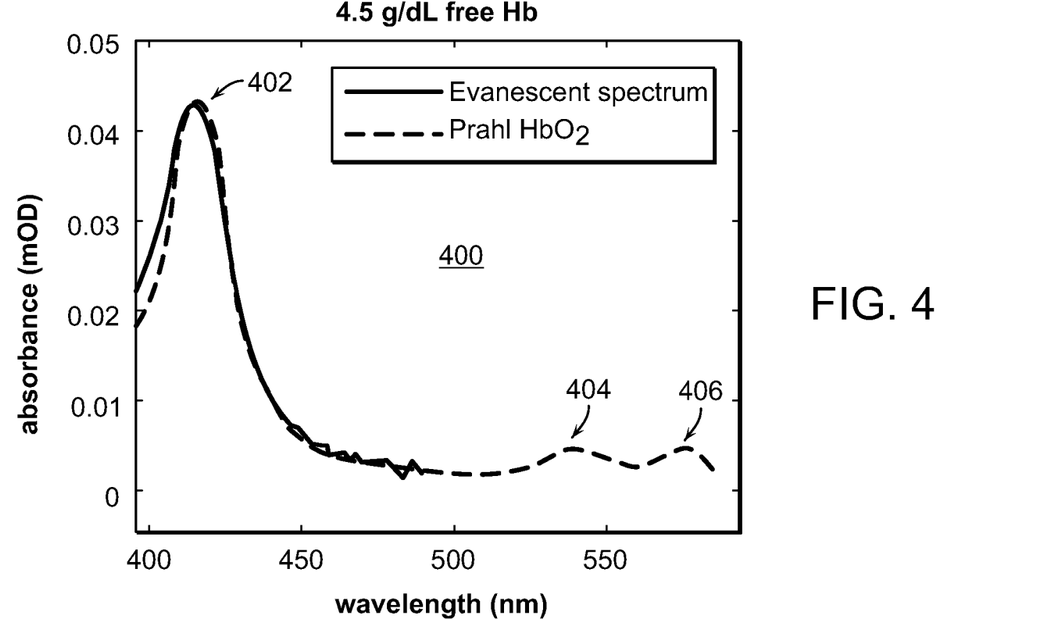
FIG. 4 is a graph showing light absorbance by a fluid sample having free hemoglobin versus wavelength of the light detected according to an aspect of the present disclosure.

FIG. 4 shows a graph 400 of light absorbance by a fluid sample having 4.5 grams per deci-liter of free hemoglobin in units of milli-optical density versus wavelength of the detected light. The graph 400 shows an absorption peak 402 of hemoglobin in the blue 410 nm-420 nm portion of the optical spectrum, which is about ten times higher than minor peaks 404 at about 540 nm and 406 at about 570 nm in the green portion of the optical spectrum, and 100 times to 1000 times higher than peaks in the red portion of the optical spectrum. Configuring the light source with a wavelength in the blue 410-420 nm range for hemolysis allows sufficient absorption of the light by hemoglobin in the narrow cell-free boundary of the channel and allows a good signal to noise ratio in the light received by the light detector.

Figure 5:
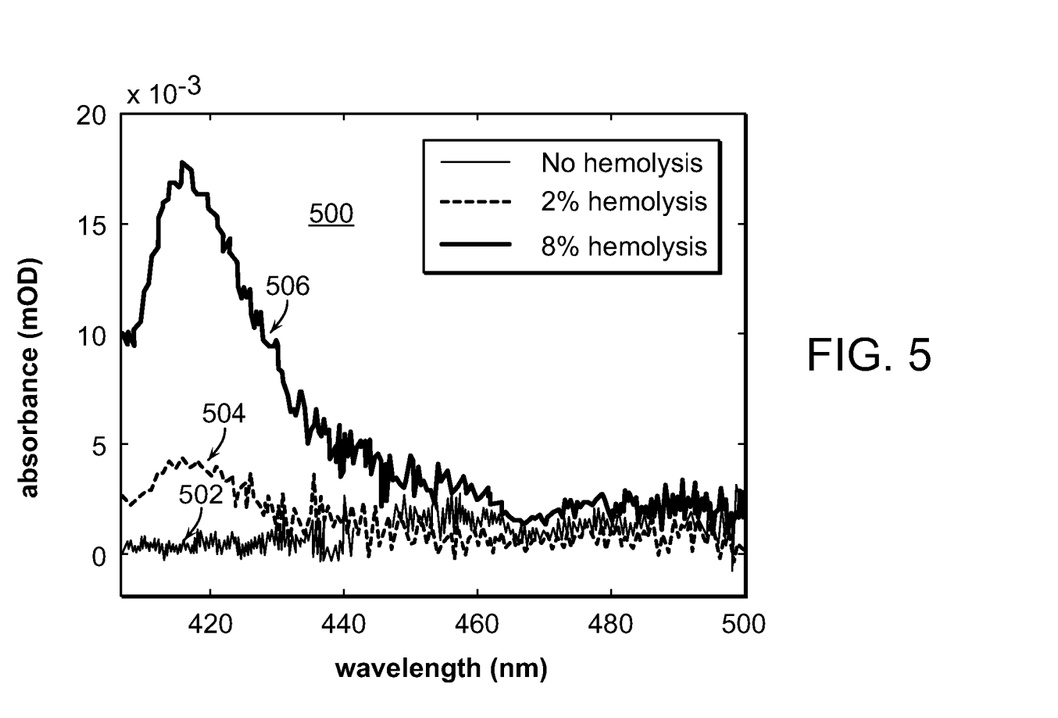
FIG. 5 is a graph showing light absorbance for three samples having different levels of hemolysis versus wavelength of light detected according to an aspect of the present disclosure.

FIG. 5 shows a graph 500 of light absorbance for three samples having different levels of hemolysis in units of milli-optical density versus wavelength of the detected light. The graph 500 shows a first signal 502 that shows no detectable peak for a sample having no hemolysis. A second signal 504 represents a sample having 2% hemolysis and has a peak of about 4 milli-optical density units in the 410 nm-420 nm range. A third signal 506 represents a sample having 8% hemolysis and has a strong peak of about 18 milli-optical density units in the 410 nm-420 nm range. This shows that detection of absorbed light in the 410 nm-420 nm range by a fluid sample is a strong indicator of an amount of an amount of hemolysis in the sample.

Figure 6:
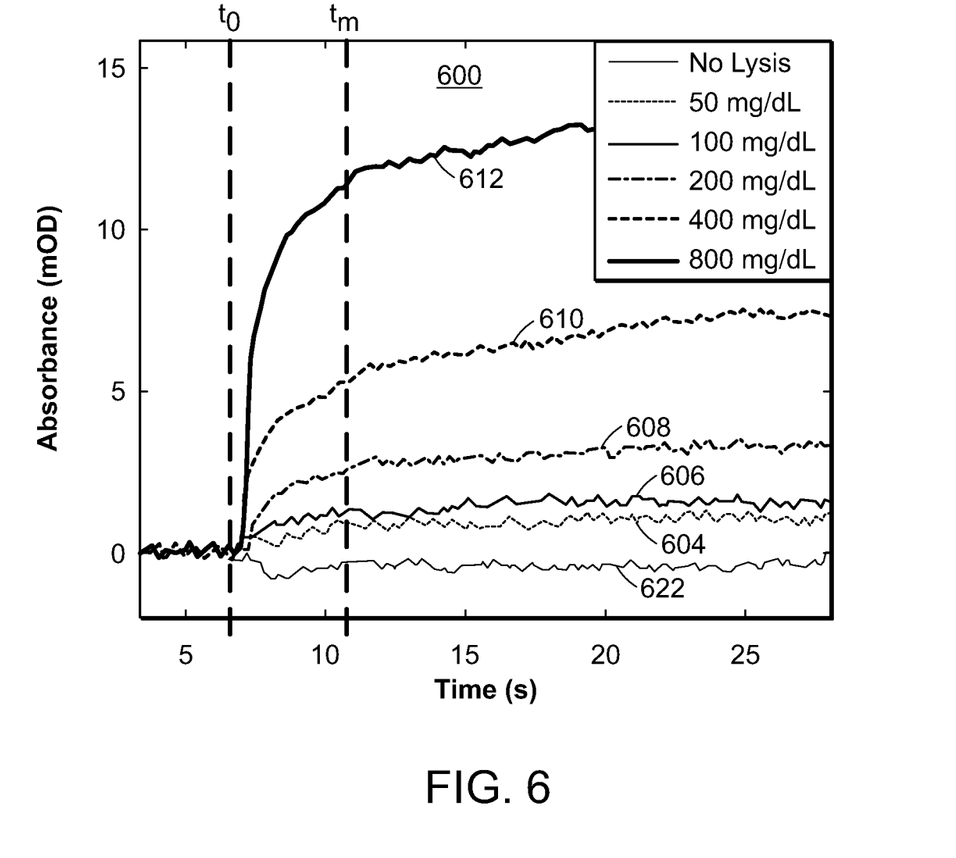
FIG. 6 a graph of absorbance versus response time for six sample of fluid having different levels of hemolysis as measured according to an aspect of the present disclosure.

FIG. 6 shows a graph 600 of absorbance in units of milli-optical density versus response time in seconds for six sample of fluid having different levels of hemolysis. The graph 600 that at a time of (tm) of measurement that is about 4 to 5 seconds after a measurement start time (t0) there is a significant separation of signal levels representing absorption in the 410-420 nm range for distinguishing different levels of hemolysis in a sample. For example at the time of measurement, a first signal 602 representing a first sample having no hemolysis indicates no absorption in the received light at wavelengths of 410 nm-420 nm. At the time of measurement a second signal 604 representing a second sample having 50 mg/dL of hemolysis indicates absorption of about 1 milli-optical density units in the received light at wavelengths of 410 nm-420 nm. At the time of measurement a third signal 606 representing a third sample having 100 mg/dL of hemolysis indicates absorption of about 1.5 milli-optical density units in the received light at wavelengths of 410 nm-420 nm. At the time of measurement a fourth signal 608 representing a fourth sample having 200 mg/dL of hemolysis indicates absorption of about 2.5 milli-optical density units in the received light at wavelengths of 410 nm-420 nm. At the time of measurement a fifth signal 610 representing a fifth sample having 400 mg/dL of hemolysis indicates absorption of about 5 milli-optical density units in the received light at wavelengths of 410 nm-420 nm. At the time of measurement a sixth signal 612 representing a sixth sample having 800 mg/dL of hemolysis indicates absorption of about 11.5 milli-optical density units in the received light at wavelengths of 410 nm-420 nm.

Figure 7:
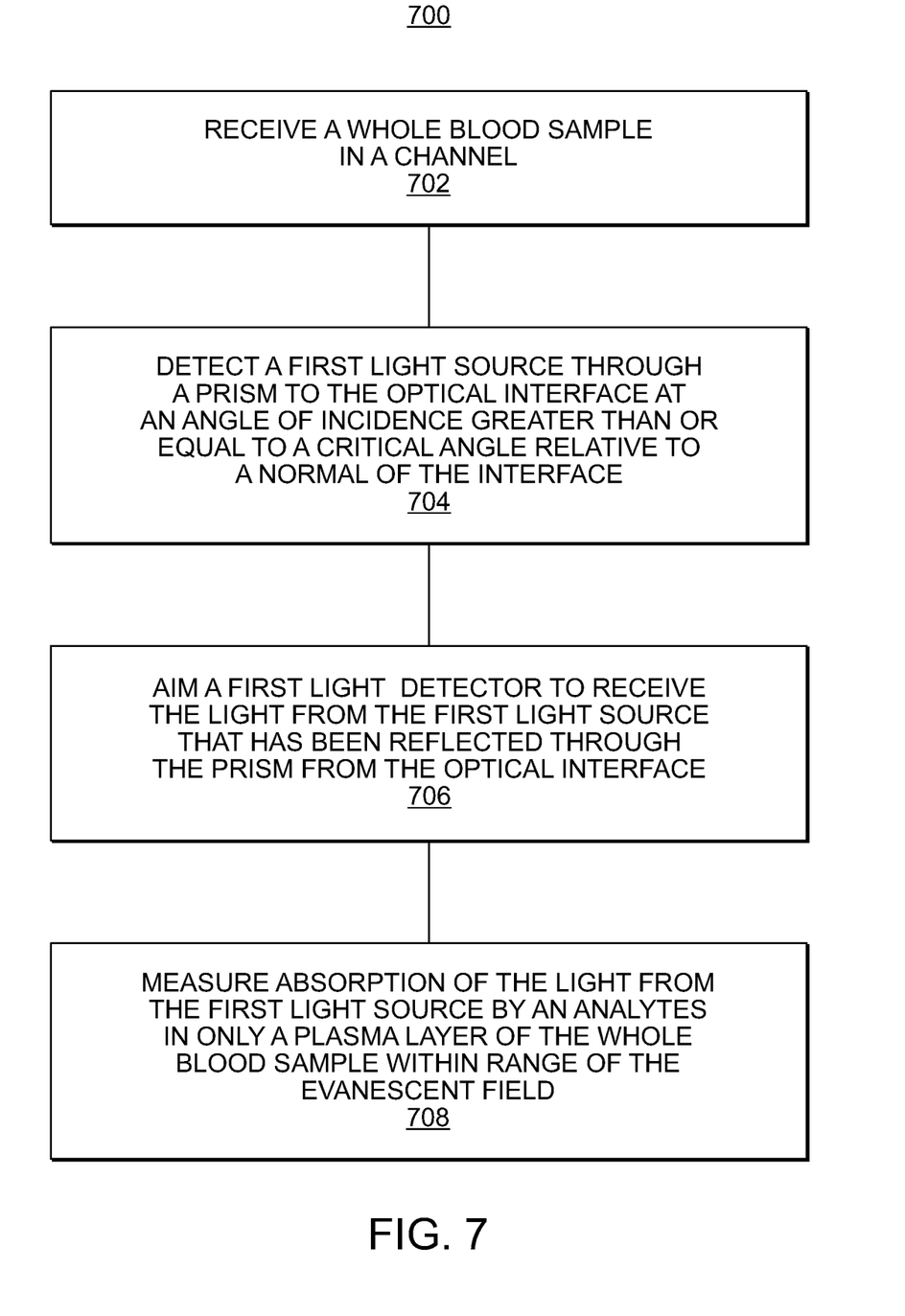
FIG. 7 is a process flow diagram describing a method for detecting analytes in whole blood without red blood cell separation from the whole blood according to an aspect of the present disclosure.

Referring to FIG. 7, another aspect of the present disclosure includes a method 700 for detecting analytes in whole blood without red blood cell separation from the whole blood. At block 702, the method 700 includes receiving a whole blood sample in a channel. A prism adjacent to the channel includes a first surface abutting the channel and defining an optical interface between the prism and the blood sample when the whole blood sample is received in the channel. At block 704, the method also includes directing a first light source through a prism to the optical interface at an angle of incidence greater than or equal to a critical angle relative to a normal of the interface. The angle of incidence creates total internal reflection of light from the first light source and creates an evanescent field extending into the channel. At block 706, the method also includes aiming a first light detector to receive the light from the first light source that has been reflected through the prism from the optical interface. At block 708, the method includes measuring absorption of the light from the first light source by an analytes in only a plasma layer of the whole blood sample within range of the evanescent field.

An apparatus for determining an analyte content in blood, according to another aspect of the present disclosure includes an optical boundary between a flowing blood sample and an optically transmissive media, such as a prism, for example. The apparatus includes an evanescent optical field in the flowing blood adjacent to the boundary, and a light detector such as a photo-diode or a spectroscope configured to detect absorption of light in the evanescent field at a wavelength corresponding to an absorption wavelength of the analyte. According to another aspect of the present disclosure, the apparatus also includes a light emitter, such as an light emitting diode or other light source, configured to direct light onto the optical boundary at a wavelength corresponding to the absorption wavelength of the analyte and at an angle of incidence selected to provide total internal reflection of the light within the optically transmissive media. According to another aspect of the present disclosure, the apparatus also includes a channel containing the flowing blood, wherein the channel is configured to generate a cell free layer of the flowing blood at a boundary of the channel, and wherein the boundary of the channel comprises the optical boundary.

In an illustrative embodiment the apparatus is configured for determining free hemoglobin content in the cell free layer of the flowing blood. In this embodiment, according to an aspect of the present disclosure, the light emitted by the light emitter has a wavelength of between 410 nanometers and 420 nanometers, and the light detector is configured to detect light absorption at wavelengths between 410 nanometers and 420 nanometers.

Although aspects of the present disclosure are described herein in the context of hemolysis, it should be understood by persons skilled in the art that aspects of the present disclosure can be implemented for detecting various analytes and other constituents in a plasma fraction of body fluid sample.

What is claimed is:

1. A method for detecting analytes in a flowing whole blood sample, the method comprising:
    directing a first light source through an optically transmissive medium to an optical interface between the optically transmissive medium and the flowing whole blood sample, wherein the optically transmissive medium is glass and wherein light from the first light source is incident at the optical interface at an angle of incidence greater than or equal to a critical angle relative to a normal of the optical interface, wherein the angle of incidence creates total internal reflection of the light from the first light source and creates an evanescent field extending into the flowing blood sample, wherein the evanescent field extends into a plasma layer of the flowing whole blood sample adjacent to the optical interface and decays to substantially zero before reaching a portion of the flowing whole blood sample containing blood cells;
    measuring absorption of the light from the first light source by an analyte in only a plasma layer of the flowing whole blood sample within the evanescent field;
    directing a second light source through optically transmissive medium to the optical interface, wherein light from the second light source has a wavelength that differs from a wavelength of the light from the first light source and wherein the light from the second light source is incident at the optical interface at second an angle of incidence greater than or equal to the critical angle relative to the normal of the optical interface, wherein the second angle of incidence creates total internal reflection of the light from the second light source and creates a second evanescent field extending into the flowing blood sample, wherein the second evanescent field extends into the plasma layer of the flowing whole blood sample adjacent to the optical interface and decays to substantially zero before reaching a portion of the flowing whole blood sample containing blood cells; and
    measuring absorption of the light from second light source by the analyte in only the plasma layer of the flowing whole blood sample within the second evanescent field.

2. The method of claim 1, comprising:
    receiving the flowing whole blood sample in a channel, wherein the optically transmissive medium adjacent to the channel includes the first surface abutting the channel, the first surface defining the optical interface between the optically transmissive medium and the flowing whole blood sample.

3. The method of claim 1, comprising:
    aiming a first light detector to receive the light from the first light source that has been reflected through the optically transmissive medium from the optical interface.

4. The method of claim 1, comprising identifying a presence of analytes in the evanescent field by comparing an intensity of the light from the first light source that has been reflected through the optically transmissive media at a first wavelength with a predetermined intensity.

5. The method of claim 4, wherein the predetermined intensity is an intensity of light emitted from the first light source.

6. The method of claim 1, comprising: comparing the absorption of light from the second light source by the analyte to the absorption of light from the first light source by the analyte to determine an absorption difference; and
    detecting the analyte in the flowing whole blood sample based on the absorption difference.

7. A method for detecting analytes in whole blood without red blood cell separation from the whole blood, the method comprising:
    receiving a whole blood sample in a channel, wherein an optically transmissive medium adjacent to the channel includes a first surface abutting the channel, the first surface defining an optical interface between the optically transmissive medium, wherein the optically transmissive medium is glass and the blood sample when the whole blood sample is received in the channel;
    directing a first light source through the optically transmissive medium to the optical interface at an angle of incidence greater than or equal to a critical angle relative to a normal of the optical interface, wherein the angle of incidence creates total internal reflection of light from the first light source and creates an evanescent field extending into the channel, wherein the evanescent field extends into a plasma layer of the blood sample adjacent to the optical interface and decays to substantially zero before reaching a portion of the channel containing blood cells;
    aiming a first light detector to receive the light from the first light source that has been reflected through the optically transmissive medium from the optical interface;
    measuring absorption of the light from the first light source by an analyte in only a plasma layer of the whole blood sample within range of the evanescent field; and
    directing a second light source through optically transmissive medium to the optical interface, wherein light from the second light source has a wavelength that differs from a wavelength of the light from the first light source and wherein the light from the second light source is incident at the optical interface at second an angle of incidence greater than or equal to the critical angle relative to the normal of the optical interface, wherein the second angle of incidence creates total internal reflection of the light from the second light source and creates a second evanescent field extending into the flowing blood sample, wherein the second evanescent field extends into the plasma layer of the flowing whole blood sample adjacent to the optical interface and decays to substantially zero before reaching a portion of the flowing whole blood sample containing blood cells; and measuring absorption of the light from second light source by the analyte in only the plasma layer of the flowing whole blood sample within the second evanescent field.

8. An apparatus for determining an analyte content in blood, the apparatus comprising:
a channel for receiving the flowing blood sample;
an optical interface between a flowing blood sample and an optically transmissive media, wherein the optically transmissive media is glass, wherein the optically transmissive medium includes a first surface abutting the channel, the first surface defining an optical interface between the optically transmissive medium and the following blood sample;
a first light source directed through the optically transmissive medium to the optical interface at an angle of incidence greater than or equal to a critical angle relative to a normal of the interface, wherein the angle of incidence creates total internal reflection of light from the first light source and creates the evanescent field extending into the channel, wherein the evanescent field extends into a plasma layer of the flowing blood sample adjacent to the optical interface and decays to substantially zero before reaching a portion of the channel containing blood cells;
a first light detector configured to detect absorption of light from the first light source in the evanescent field at a first wavelength corresponding to an absorption wavelength of the analyte;
a second light source directed through optically transmissive medium to the optical interface, wherein light from the second light source has a second wavelength that differs from a first wavelength of the light from the first light source and wherein the light from the second light source is incident at the optical interface at a second an angle of incidence greater than or equal to the critical angle relative to the normal of the optical interface, wherein the second angle of incidence creates total internal reflection of the light from the second light source and creates a second evanescent field extending into the flowing blood sample, wherein the second evanescent field extends into the plasma layer of the flowing whole blood sample adjacent to the optical interface and decays to substantially zero before reaching a portion of the flowing whole blood sample containing blood cells; and
a second light detector configured to detect absorption of light from the second light source in the evanescent field at the second wavelength corresponding to the absorption wavelength of the analyte.

9. The apparatus of claim 8, wherein the optically transmissive media comprises a prism.

10. The apparatus of claim 9, wherein the first light source comprise a light emitting diode.

11. The apparatus of claim 9, wherein the first light source comprises a laser diode.

12. The apparatus of claim 9, wherein the first light source is configured to direct light onto the optical interface at a wavelength corresponding to the absorption wavelength of the analyte, and wherein the angle of incidence is selected to provide total internal reflection of the light within the optically transmissive media.

13. The apparatus of claim 8, wherein the first light detector aimed to receive the light from the first light source that has been reflected through the optically transmissive medium from the optical interface.

14. The apparatus of claim 13, wherein the light detector comprises a photo-diode.

15. The apparatus of claim 8, wherein the channel is configured to generate a cell free layer of the of the flowing blood at a the optical interface of the channel.

16. The apparatus of claim 8, wherein the analyte comprises free hemoglobin in the cell free layer of the flowing blood.

17. The apparatus of claim 16, wherein the light emitted by the light emitter has a wavelength of between 410 nanometers and 420 nanometers.

18. The apparatus of claim 17, wherein the light detector is configured to detect light absorption at wavelengths between 410 nanometers and 420 nanometers.

* * * * *